(12) United States Patent
Westermann

(10) Patent No.: US 9,220,649 B2
(45) Date of Patent: Dec. 29, 2015

(54) ELECTRIC ACTUATOR SYSTEM

(75) Inventor: Karsten Westermann, Sønderborg (DK)

(73) Assignee: Linak A/S (DK)

( * ) Notice: Subject to any disclaimer, the term of this patent is extended or adjusted under 35 U.S.C. 154(b) by 4 days.

(21) Appl. No.: 14/006,185

(22) PCT Filed: Apr. 12, 2012

(86) PCT No.: PCT/DK2012/000040
§ 371 (c)(1),
(2), (4) Date: Sep. 19, 2013

(87) PCT Pub. No.: WO2012/139578
PCT Pub. Date: Oct. 18, 2012

(65) Prior Publication Data
US 2014/0000031 A1    Jan. 2, 2014

(30) Foreign Application Priority Data
Apr. 12, 2011  (DK) ................. 2011 00289

(51) Int. Cl.
*A61G 7/018* (2006.01)
*A61G 7/012* (2006.01)
*A61B 5/11* (2006.01)
*A61G 7/015* (2006.01)
*H02K 7/00* (2006.01)
*H02K 11/00* (2006.01)

(52) U.S. Cl.
CPC .............. *A61G 7/012* (2013.01); *A61B 5/1115* (2013.01); *A61G 7/015* (2013.01); *A61G 7/018* (2013.01); *H02K 7/00* (2013.01); *H02K 11/001* (2013.01); *A61G 2203/44* (2013.01)

(58) Field of Classification Search
CPC ..................................... A61G 7/018
USPC ................. 5/616–619, 611, 600, 613
See application file for complete search history.

(56) References Cited

U.S. PATENT DOCUMENTS

| 4,934,468 | A | 6/1990 | Koerber et al. |
| 5,276,432 | A * | 1/1994 | Travis ........................ 340/573.4 |
| 6,897,780 | B2 | 5/2005 | Ulrich et al. |
| 7,066,041 | B2 | 6/2006 | Nielsen |
| 8,272,087 | B2 | 9/2012 | Westermann |
| 8,381,336 | B2 | 2/2013 | Kazuno et al. |
| 8,555,431 | B2 | 10/2013 | Nielsen |
| 2009/0044340 | A1 * | 2/2009 | Nielsen ............................ 5/618 |
| 2010/0005590 | A1 * | 1/2010 | Jensen ............................ 5/611 |

FOREIGN PATENT DOCUMENTS

GB            2390062         12/2003

* cited by examiner

*Primary Examiner* — Fredrick Conley
(74) *Attorney, Agent, or Firm* — Dykema Gossett PLLC

(57) ABSTRACT

An electric actuator system for hospital and care beds comprising at least one linear actuator (9,48) for adjusting the lying surface of the bed. The actuator (9,48) used for adjusting the backrest section (6,57) of the bed comprises means for registering the force which it is exposed to. By comparing the registered forces to a zero value and/or a force interval, it can be determined whether the person occupying the bed is in the process of leaving the bed or has already left the bed. A connected alarm can thus notify the staff that the bed-bound person is in the process of leaving the bed.

12 Claims, 4 Drawing Sheets

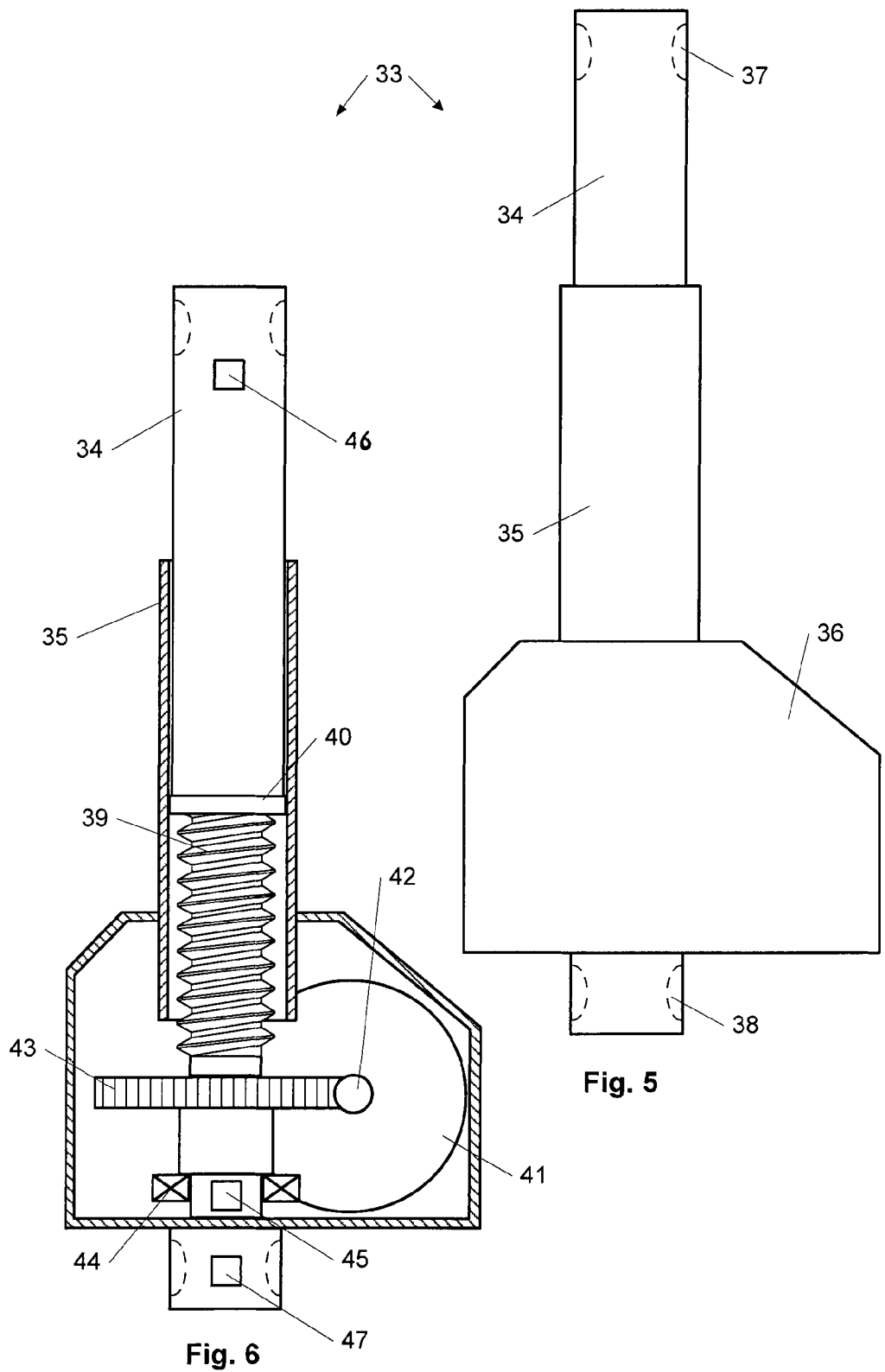

ELECTRIC ACTUATOR SYSTEM

BACKGROUND OF THE INVENTION

1. Field of the Invention

The invention relates to an electric actuator system for hospital and care beds.

2. The Prior Art

The actuator system is according to the invention of the type which can be used for adjusting a hospital or care bed. In this type of bed the mattress is carried by a support surface having an adjustable backrest and legrest section, said support surface being mounted in a bed frame which may be raised and lowered by means of linear actuators in the actuator system. Further, the backrest and legrest sections of the bed may be adjusted by means of linear actuators. Normally, a type of linear actuator comprising a thrust rod, e.g. of the type described in WO 02/29284 A1 Linak A/S is used. This type of linear actuator comprises a spindle with a spindle nut. The spindle is driven by a reversible electric motor through a transmission. When the spindle is driven, the spindle nut is moved in an inwards or outwards direction depending on the direction of rotation of the electric motor. The linear actuator is a separate product with the spindle, transmission and electric motor enclosed in a housing. The housing typically consists of a motor housing and an outer tube. An inner tube is secured to the spindle nut. The inner tube is displaced in and out of the outer tube as the spindle nut is moved in and out on the spindle. In the opposite end of the spindle nut the inner tube comprises a front mounting. The outer side of the motor housing is furnished with a rear mounting. The front mounting and rear mounting are used to secure the linear actuator in the structure which should be adjusted.

For certain patients in the hospital and care sector it is necessary for the nursing staff to know whether the patient is in the process of leaving the bed or has left the bed. Such a bed is i.a. described in U.S. Pat. No. 4,934,468 Hill Rom Co. Inc. and U.S. Pat. No. 5,276,432 Stryker Corp. These hospital beds are equipped with a weighing system for weighing and/or monitoring the patient's weight. The weighing system can however also be configured to monitor the patient's position in the bed. The weighing system can further be connected to an alarm which can give off a signal in case the patient assumes a position where it is conceivable that the patient may leave the bed or has already left the bed. A bed having similar characteristics is described in EP 1 974 708 A1 Paramount. Here, changes in the patient's center of gravity are registered by a number of interconnected weight sensors located at each corner of the lying surface of the bed. By comparing the readings from each weight sensor, it can be detected whether a patient is sitting up and is thus potentially in the process of leaving the hospital bed, but naturally also whether the patient has left the bed.

Common for these types of bed structures is that they are intended for continuous weighing for accurate supervision of the patient's weight. In order to be able to do this with a sufficient accuracy high-end sensor with a high resolution are used. This fact is thus also reflected in the price of these bed structures, which are very expensive. The use of these beds is thus also limited to a select few patients requiring special treatment and special care.

A far simpler and cheaper construction is described in WO 2009/021513 A1 Linak A/S, which discloses an electromechanical linear actuator comprising the same elements as the electro mechanical linear actuator described in the preamble. Furthermore, this type of actuator comprises means for registering forces on the actuator. Means for registering these forces may be a load cell, such as a strain gauge or a piezo element. By registering the relative changes to the force on each actuator it can be determined whether a person is in the process of leaving a bed or has already left the bed. It is therefore the load of the person occupying the bed which is registered along with the position and position changes of the person in the bed. Although this construction as a whole constitutes a simpler solution than the solutions described above it is desired to provide an even simpler actuator system for a hospital or care bed which can detect whether a person is in the process of leaving the bed or has left the bed.

SUMMARY OF THE INVENTION

The actuator system according to the invention is characterized in that the force solely is registered by the linear actuator used for adjusting the backrest section of the bed. Thus, only this actuator is used for determining whether the person occupying the bed is in the process of leaving the bed or has already left the bed. This is therefore primarily determined based on the load of the person's torso. Hereby, a simple and very inexpensive actuator system is provided which can be mounted both on newly fabricated beds or retrofitted on already existing beds. Whether the person occupying the bed has left the bed is detected by comparing the registered force to a given zero value determined by the actuator system.

In a special embodiment of the existing actuator system the registered forces is compared to a force interval calculated by the actuator system. If this interval is exceeded this can indicate a state of a patient which requires the attention of the nursing staff.

In a further embodiment the electric actuator system does not compare the registered force to the given zero value or the calculated force interval during the adjustment of the bed. This ensures that the actuator system does not give off an unintended alarm signal during the adjustment of the bed.

In yet another embodiment the actuator system calculates a new force interval after adjustment of the backrest section. The calculation of the interval can be conducted by a microprocessor comprised by the actuator system.

In an embodiment the electric actuator system further comprises at least one actuator for raising and lowering the bed frame of the hospital and care bed where the actuator comprises means for registering the force thereon.

The control box in the electric actuator system may further comprise a mains based power supply and a rechargeable battery pack. Hereby, the actuator system can be operated in a given period of time without being connected to mains.

In an embodiment the electric actuator system can comprise a transceiver, by which an alarm signal can be wireless transmitted to the nursing staff via their paging system or alarm system.

The invention further relates to a hospital or care bed comprising an actuator system of the type described above. The bed may be a hospital, care or elevation bed.

BRIEF DESCRIPTION OF THE DRAWINGS

An embodiment of the actuator system according to the invention will be described more fully below with reference to the accompanying drawings, in which FIG. 5 shows a linear actuator comprising a load cell, FIG. 6 shows the linear actuator in FIG. 5 where the motor housing and the outer tube has been partially removed.

DETAILED DESCRIPTION OF THE PREFERRED EMBODIMENT

Figure 1:
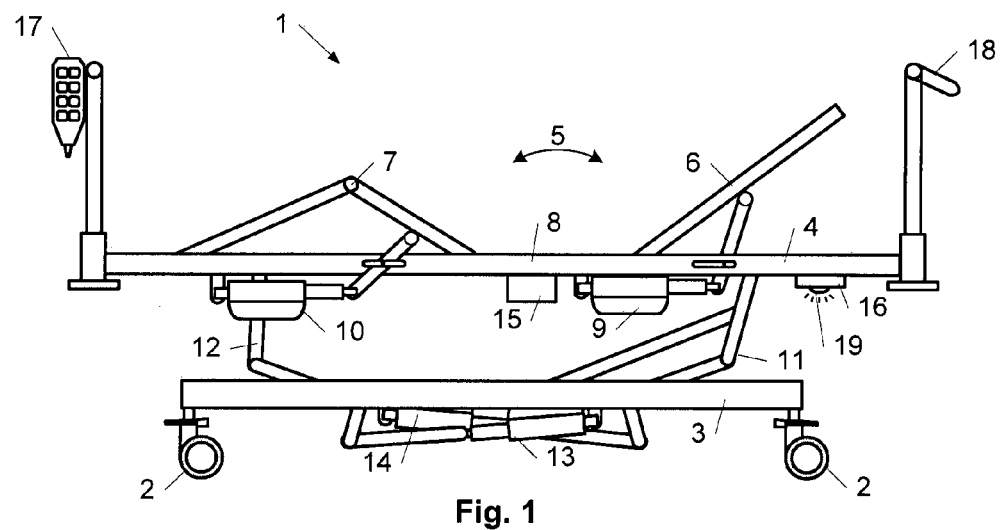
FIG. 1 shows a schematic view of a hospital or care bed comprising an actuator system in a first embodiment.

FIG. 1 shows a hospital bed 1 comprising an under frame 3 equipped with drive wheels 2 and an upper frame 4. An adjustable support surface 5 for a mattress (not shown) is mounted to the upper frame 4. The supporting surface comprises a backrest section 6, an articulated legrest section 7 and a fixed middle section 8 there between. The backrest and legrest sections 6,7 can be adjusted with an actuator 9, 10 each such that the supporting surface may assume different contours. The upper frame 4 is connected to the under frame 2 with a linkage 11,12 at each end. The upper frame 4 may be raised and lowered by means of a pair of actuators 13,14 connected to the linkages 11,12. All the actuators 9,10,13,14 are connected to a control box 15 comprising a control. The control box can be connected to mains and may e.g. be equipped with a power supply. The control box may further comprise a rechargeable battery pack.

A junction box 16 is connected to the control box 15 for connecting one or more control units, such as a hand control 17 and a control panel 18 integrated in the head or foot board, and possibly other peripheral equipment. The overall system comprising actuators 9,10,13,14, control box 15 and control units 17,18 is known as an actuator system.

The actuator 9 for adjusting the backrest section contains means for registering the forces which it is exposed to, as a result of the load of the person lying in the bed. This type of actuator is disclosed in WO 2009/021513 A1 Linak A/S and the document is hereby made part of the present application. Thus, this actuator 9 alone is used to determine whether the person occupying the bed is in the process of leaving the bed or has already left the bed. This is thus primarily determined based on the load of the person's torso. Hereby, a simple and very inexpensive actuator system is provided which may be mounted on newly fabricated beds or retrofitted on already existing beds. Whether the person occupying the bed has left the bed can be determined by comparing the registered force to a given zero value and/or force interval calculated by the actuator system. The interval is calculated based on the force registered in the actuator. In case the subsequent registrations of the force on the actuator fall outside the calculated interval a message or alarm can be sent e.g. to the nursing staff. During adjustment of the bed by activation of one or more of the actuator system's actuators 9,10,13,14, the registered force is not compared to the calculated interval. This is owing to the fact that the registered force will change as a result of the changed adjustment of the bed. For the backrest 6 the registered force will thus be different depending on the angle of the backrest section 6 and how the actuator is placed compared to the backrest section 6. Therefore, the actuator system recalculates a new force interval after an ended adjustment of the bed 1 based on the new registered force. The calculation of the force interval can e.g. be conducted by a micro processor 23 which e.g. can be a part of the control box 18 of the actuator system.

Figure 2:
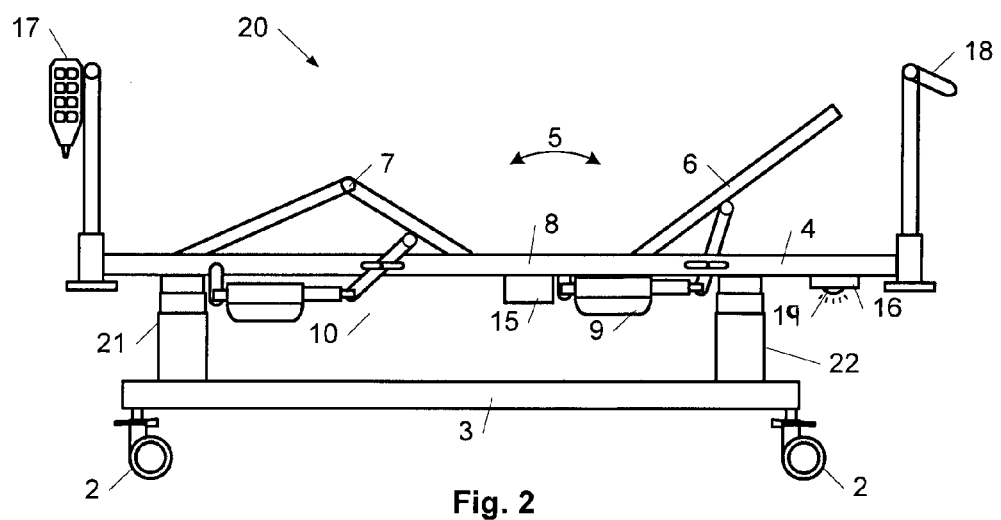
FIG. 2 shows a schematic view of a hospital or care bed comprising an actuator system in a second embodiment.

FIG. 2 shows a schematic view of a hospitals and care bed 20 in another embodiment than the bed shown in FIG. 1. Here, the under frame 3 and the upper frame 4 are not connected by linkages but are instead connected by two linear actuators designed as lifting columns 21,22.

Figure 3:
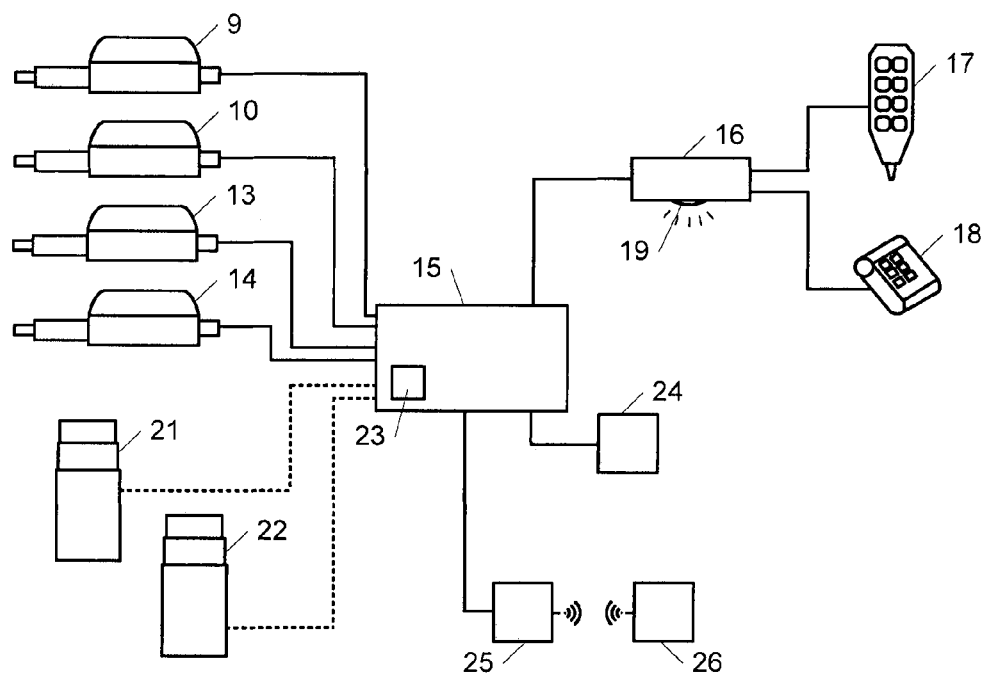
FIG. 3 shows a block diagram of the actuator system in the beds shown in FIGS. 1 and 2.

FIG. 3 shows a block diagram of the actuator system in the beds shown in FIGS. 1 and 2. When the patient sits up in the bed and thus potentially could be in the process of leaving the bed or has already left the bed, these changes are registered in the actuator 9. The information concerning these changes is sent to the control box 15. A microprocessor 23 in the control box can thus determine if an alarm should be generated based on these changes either in connection with the bed or to the nursing staff. If the alarm is generated in connection with the bed 1,20 this can occur via an auditory, visual or tactile alarm connected to the actuator system or integrated in the actuator system. The latter could e.g. be in connection with the control box 15 and/or the control unit 17,18. In case the alarm should be sent to the nursing staff or another person, capable of attending to the patient this can be done by connecting the actuator system to the paging system or alarm system used in the given hospital or nursing home. This connection to the actuator system can be achieved in various ways depending on the paging system or alarm system in the given hospital or nursing home. Furthermore, the connection may be cabled and/or wireless. In case the connection is cabled, this can e.g. be done via a cable running from the control box 15 to a wall-mounted plug 24 in the proximity of the bed. If the connection is wireless, the control box 15 generates a signal, which through a transceiver 25 is sent to the paging system or alarm system used in the given hospital or nursing home via the transceiver 26.

The control box 15 can thus convert information from the load cell in the linear actuator 9 into a signal adapted to the communications protocol used by the paging system or alarm system. The transceiver 24 may e.g. be incorporated in the control box 15 or in the junction box 16.

Figure 4:
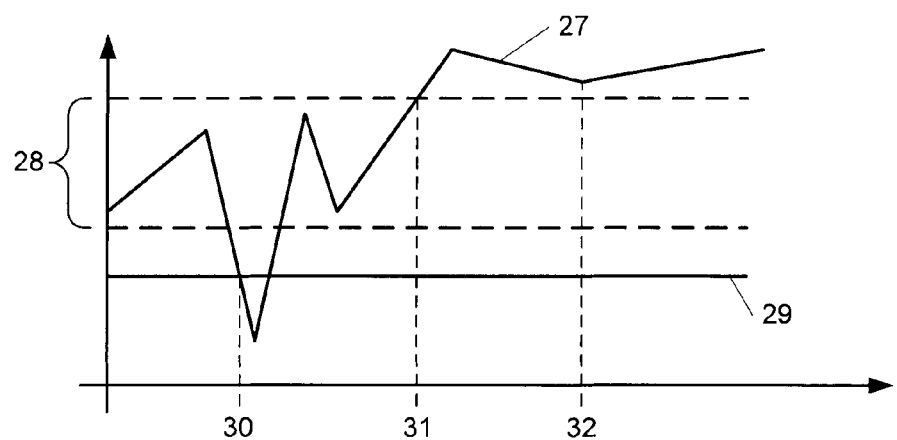
FIG. 4 shows a graph of the deflection of a registered force seen over time.

FIG. 4 shows a graph of the deflection of a registered force 27 (ordinate axis) seen over time (abscissa axis) compared to a calculated force interval 28 and a zero value 29. If the registered force 27 drops below the zero value 29 the patient is no longer in the bed. In this situation 30 the actuator system will give off an alarm as described under FIG. 3. Based on the registered force 27 which the patient exerts on the actuator 9 at a given adjustment of the bed, the actuator system can calculate a force interval 28. This interval indicates the tolerable changes to the force 27 on the actuator 9 as a result of the patient's movement in the bed. The limits of the interval can be defines depending on the state of the patient and the type of care of the patient. If the registered force falls outside the limits of the interval in e.g. a given time interval 31,32, this can be an indicator of changes in the state of health of which the nursing staff must be informed or alerted. It could also be an indicator that the patient is in a position where he could be in the process of leaving the bed.

FIG. 5 shows a linear actuator 33 of the type described in the preamble comprising a thrust rod and is thus of the same type as the linear actuators 9,10,13,14. The thrust rod is also known as an inner tube 34. The linear actuator comprises an outer tube 35 and a motor housing 36. The linear actuator 33 further comprises a front mounting 37 at the outer end of the inner tube 34 and a rear mounting 38 at the motor housing 36.

FIG. 6 shows the linear actuator in FIG. 5, where the motor housing 36 and the outer tube 35 has been partly removed.

The main components of the linear actuator 33 are a spindle unit consisting of a spindle 39, on which a spindle nut 40 is arranged. The spindle nut 40 may be secured against rotation. The inner tube 34 is secured to the spindle nut 40 and may thus be moved inwards or outwards on the outer tube 35 depending on the direction of rotation of the spindle 39. The spindle 39 is driven by a reversible electric motor 42 through a transmission. The transmission here comprises a worm 42 located in extension of the drive shaft 42 of the electric motor, and a worm wheel 43 secured to the spindle 39. Moreover, a bearing 44 is secured to the spindle 39. The bearing 44 may e.g. be a ball bearing or a roller bearing. The linear actuator 33 comprises a load cell 45 for registering the force, which the linear actuator 33 is exposed to and the relative changes to this force. In FIG. 6 the load cell 45 is located in connection with the rear part of the spindle 39. The load cell may also be arranged in connection with the inner tube or the rear mounting as indicated with reference numerals 46 and 47. The load cell 45,46, 47 may e.g. be a strain gauge or a piezo element. The linear actuator 33 is connected to a control box 15 of the type described in connection with FIGS. 1-4. The information concerning the force on the linear actuator 33 or a change will thus be transmitted to the control box 15. The linear actuator 33 is, as stated above, disclosed in WO 2009/021513 A1 Linak A/S.

The linear actuator 33 shown in FIGS. 5 and 6 only discloses the main components. Thus, the linear actuator 33 may be equipped with e.g. a brake mechanism, additional bearings, release mechanism, etc.

It is noted that the invention further may be used in connection with so-called dual actuators comprising two spindle units and a control box in one common housing. This type is further described in WO 2007/093181 A1 Linak A/S.

Figure 7:
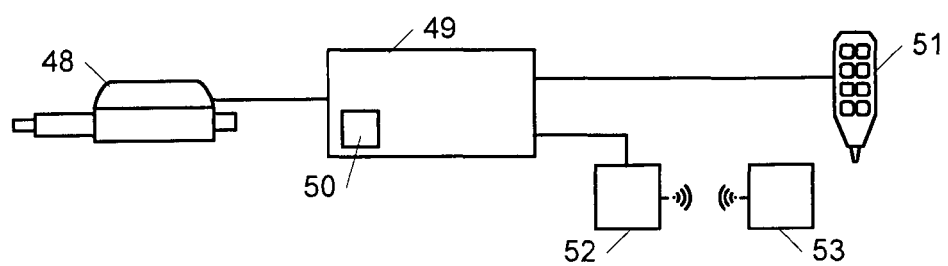
FIG. 7 shows a simple actuator system according to the invention.

FIG. 7 shows a simplified actuator system according to the invention. Here, the actuator comprises a single linear actuator 48 of the type described in connection with FIGS. 5 and 6. The linear actuator 48 is connected to a control box 49. The control box 49 comprises a micro processor 50 and functions as described in connection with FIGS. 1-6. The actuator system comprises a control unit 51 which likewise is connected to the control box 49 The actuator system further comprises means for directly or indirectly generating an alarm in case the force on the linear actuator 48 falls outside the determined or calculated force interval as described in connection with FIGS. 1-4. The actuator system shown in FIG. 7 comprises means for indirectly generating an alarm. Thus, the actuator system comprises a transceiver 52 connected to the control box 49. The transceiver 52 functions as described in connection with FIG. 3. I.e. the transceiver 52 can send a wireless alarm signal to a transceiver 53 comprised by the paging system or alarm system installed in the given hospital or nursing home.

Figure 8:
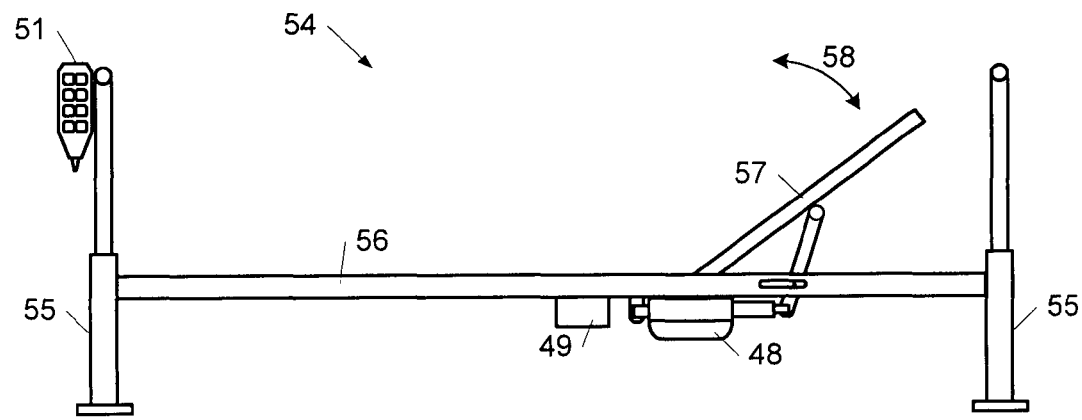
FIG. 8 shows an elevation bed comprising the actuator system shown in FIG. 7.

FIG. 8 shows a simple elevation bed 54 having the actuator system shown in FIG. 7 mounted. The elevation bed 54 comprises a pair of legs 55 carrying a frame 56. The frame comprises a lying surface on which a mattress (not shown) can be arranged. The slope of the backrest section 57 of the bed compared to the horizontal axis of the bed can be adjusted by means of the linear actuator 48, see the arrow 58.

The invention claimed is:

1. An electric actuator system for a hospital and care bed which includes a bed frame and an adjustable backrest section, said actuator system comprising:
    an electromechanical linear actuator for adjusting the backrest section of the bed, the actuator including means for registering force thereon and relative changes in said force,
    a control box connected to the actuator,
    at least one control unit,
    and means for comparing the force solely registered by said actuator with a zero value to determine whether a person is leaving or has already left the bed.

2. The electric actuator system for hospital and care beds according to claim 1, wherein the actuator system compares the registered force to a force interval calculated by the actuator system.

3. The electric actuator system for hospital and care beds according to claim 2, wherein the actuator system comprises a microprocessor for calculating the force interval.

4. The electric actuator system for hospital and care beds according to claim 1, wherein the actuator system during adjustment of the backrest section does not compare the registered force to the zero value or the calculated force interval.

5. The electric actuator system for hospital and care beds according to claim 4, wherein the actuator system after adjusting the backrest section makes a new calculation of the force interval.

6. The electric actuator system for hospital and care beds according to claim 1, wherein the actuator system further comprises at least one linear actuator having means for registering the force thereon, where the linear actuator is used for raising and lowering the bed frame of the hospital and care bed.

7. The electric actuator system for hospital and care beds according to claim 1, wherein the control box comprises a mains based power supply.

8. The electric actuator system for a hospital and care bed according to claim 1, wherein the control box comprises a rechargeable battery pack.

9. The electric actuator system for a hospital and care bed according to claim 1, wherein the actuator system comprises a transceiver.

10. A bed comprising an actuator system according to claim 1.

11. The bed according to claim 10, where the bed is a hospital or care bed.

12. The bed according to claim 10, whether the bed is an elevation bed.

* * * * *

UNITED STATES PATENT AND TRADEMARK OFFICE
CERTIFICATE OF CORRECTION

PATENT NO. : 9,220,649 B2
APPLICATION NO. : 14/006185
DATED : December 29, 2015
INVENTOR(S) : Westermann It is certified that error appears in the above-identified patent and that said Letters Patent is hereby corrected as shown below:

In The Claims
Column 6, line 53 (Claim 12), delete "whether" and insert --where--

Signed and Sealed this
Fifteenth Day of March, 2016

Michelle K. Lee
*Director of the United States Patent and Trademark Office*